United States Patent
Eriksen et al.

(10) Patent No.: US 8,618,099 B2
(45) Date of Patent: Dec. 31, 2013

(54) PYRAZOLYL-PYRIMIDINE DERIVATIVES AND THEIR USE AS POTASSIUM CHANNEL MODULATORS

(75) Inventors: Birgitte L. Eriksen, Farum (DK); Charlotte Hougaard, Bagsværd (DK); Dan Peters, Malmö (SE); Palle Christophersen, Ballerup (DK)

(73) Assignee: Ataxion, Inc., Cambridge, MA (US)

( * ) Notice: Subject to any disclaimer, the term of this patent is extended or adjusted under 35 U.S.C. 154(b) by 177 days.

(21) Appl. No.: 13/061,347

(22) PCT Filed: Aug. 26, 2009

(86) PCT No.: PCT/EP2009/060973
§ 371 (c)(1),
(2), (4) Date: Jun. 2, 2011

(87) PCT Pub. No.: WO2010/026087
PCT Pub. Date: Mar. 11, 2010

(65) Prior Publication Data
US 2011/0230484 A1 Sep. 22, 2011

Related U.S. Application Data
(60) Provisional application No. 61/094,142, filed on Sep. 4, 2008.

(30) Foreign Application Priority Data
Sep. 2, 2008 (DK) .................................. 2008 01219

(51) Int. Cl.
*A61K 31/535* (2006.01)
*C07D 413/02* (2006.01)

(52) U.S. Cl.
USPC ........................................ 514/235.8; 544/122

(58) Field of Classification Search
None
See application file for complete search history.

(56) References Cited

U.S. PATENT DOCUMENTS

| | | |
|---|---|---|
| 2008/0275045 A1 | 11/2008 | Eriksen et al. |
| 2009/0036475 A1 | 2/2009 | Eriksen et al. |
| 2009/0306102 A1 | 12/2009 | Eriksen et al. |
| 2009/0325989 A1 | 12/2009 | Eriksen et al. |
| 2010/0035934 A1 | 2/2010 | Eriksen et al. |
| 2010/0105705 A1 | 4/2010 | Eriksen et al. |
| 2010/0120797 A1 | 5/2010 | Eriksen et al. |
| 2010/0130516 A1 | 5/2010 | Eriksen et al. |
| 2010/0152210 A1 | 6/2010 | Eriksen et al. |
| 2012/0004246 A1 | 1/2012 | Eriksen et al. |

FOREIGN PATENT DOCUMENTS

| | | |
|---|---|---|
| WO | WO 03/075828 A2 | 9/2003 |
| WO | WO 2005/099711 A1 | 10/2005 |
| WO | WO 2006/100212 A1 | 9/2006 |
| WO | WO 2008/092942 A2 | 8/2008 |

OTHER PUBLICATIONS

International Search Report, PCT/EP2009/060973, Dec. 11, 2009.

*Primary Examiner* — Jason M Nolan
*Assistant Examiner* — Ana Z Muresan
(74) *Attorney, Agent, or Firm* — Birch, Stewart, Kolasch & Birch, LLP.

(57) ABSTRACT

This invention relates to novel pyrazolyl-pyrimidine derivatives and their use as potassium channel modulating agents. In another aspect the invention is directed to pharmaceutical compositions useful for the treatment or alleviation of diseases or disorders associated with the activity of potassium channels.

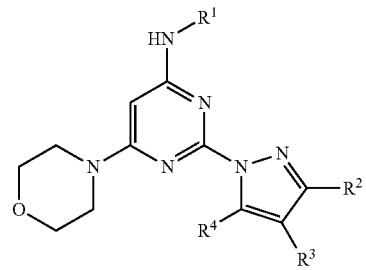

5 Claims, No Drawings

PYRAZOLYL-PYRIMIDINE DERIVATIVES AND THEIR USE AS POTASSIUM CHANNEL MODULATORS

This application is the National Phase of PCT/EP2009/060973 filed on Aug. 26, 2009, which claims priority under 35 U.S.C. 119(e) to U.S. Provisional Application No. 61/094,142 filed on Sep. 4, 2008 and under 35 U.S.C. 119(a) to Patent Application No. PA 2008 01219 filed in Denmark on Sep. 2, 2008, all of which are hereby expressly incorporated by reference into the present application.

TECHNICAL FIELD

This invention relates to novel pyrazolyl-pyrimidine derivatives and their use as potassium channel modulating agents. Moreover the invention is directed to pharmaceutical compositions useful for the treatment or alleviation of diseases or disorders associated with the activity of potassium channels.

BACKGROUND ART

Ion channels are transmembrane proteins, which catalyse the transport of inorganic ions across cell membranes. The ion channels participate in processes as diverse as the generation and timing of action potentials, synaptic transmissions, secretion of hormones, contraction of muscles, etc.

All mammalian cells express potassium ($K^+$) channels in their cell membranes, and the channels play a dominant role in the regulation of the membrane potential. In nerve and muscle cells they regulate the frequency and form of the action potential, the release of neurotransmitters, and the degree of broncho- and vasodilation.

From a molecular point of view, the $K^+$ channels represent the largest and most diverse group of ion channels. For an overview they can be divided into five large subfamilies: Voltage-activated $K^+$ channels ($K_v$), long QT related $K^+$ channels (KvLQT), inward rectifiers ($K_{IR}$), two-pore $K^+$ channels ($K_{TP}$), and calcium-activated $K^+$ channels ($K_{ca}$).

The latter group, the $Ca^{2+}$-activated $K^+$ channels, consists of three well-defined subtypes: SK channels, IK channels and BK channels. SK, IK and BK refer to the single-channel conductance (Small, Intermediate and Big conductance K channel). The SK, IK, and BK channels exhibit differences in e.g. voltage- and calcium-sensitivity, pharmacology, distribution and function.

SK channels are present in many central neurons and ganglia, where their primary function is to hyperpolarize nerve cells following one or several action potentials, in order to prevent long trains of epileptogenic activity to occur. The SK channels are also present in several peripheral cells including skeletal muscle, gland cells, liver cells, and T-lymphocytes. The significance of SK channels in normal skeletal muscle is not clear, but their number is significantly increased in denervated muscle, and the large number of SK channels in the muscle of patients with myotonic muscle dystrophia, suggest a role in the pathogenesis of the disease.

Studies indicate that $K^+$ channels may be a therapeutic target in the treatment of a number of diseases including asthma, cystic fibrosis, chronic obstructive pulmonary disease and rhinorrhea, convulsions, vascular spasms, coronary artery spasms, renal disorders, polycystic kidney disease, bladder spasms, overactive bladder, urinary incontinence, bladder outflow obstruction, interstitiel cystitis, irritable bowel syndrome, gastrointestinal dysfunction, secretory diarrhoea, ischaemia, cerebral ischaemia, ischaemic heart disease, angina pectoris, coronary heart disease, traumatic brain injury, Parkinson's disease, dyskinesia, psychosis, anxiety, depression, dementia, memory and attention deficits, Alzheimer's disease, dysmenorrhea, narcolepsy, Reynaud's disease, intermittent claudication, Sjogren's syndrome, migraine, pain, arrhythmia, hypertension, absence seizures, myotonic muscle dystrophia, xerostomi, diabetes type II, hyperinsulinemia, premature labour, hair loss, cancer and immune suppression.

SUMMARY OF THE INVENTION

It is an object of the present invention to provide novel pyrazolyl-pyrimidine compounds capable of modulating SK channels, or subtypes of SK channels.

In one aspect, the present invention provides a compound of formula (I)

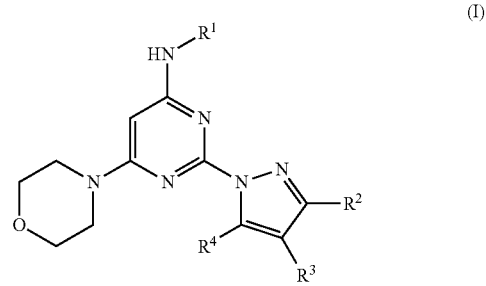

(I)

any of its stereoisomers or any mixture of its stereoisomers, or a pharmaceutically acceptable salt thereof, wherein $R^1$, $R^2$, $R^3$ and $R^4$ are as described below.

In another aspect, the invention provides pharmaceutical compositions comprising an effective amount of a compound of the invention.

In further aspects the invention relates to the use of a derivative of the invention for the manufacture of a medicament for the treatment or alleviation of diseases or disorders associated with the activity of potassium channels, and to method of treatment or alleviation of disorders or conditions responsive to modulation of potassium channels.

DETAILED DISCLOSURE OF THE INVENTION

In one aspect, the present invention provides compounds of formula (1)

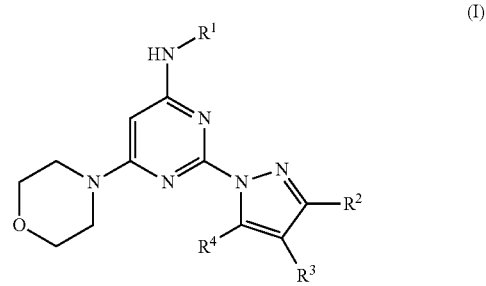

(I)

any of its stereoisomers or any mixture of its stereoisomers, or a pharmaceutically acceptable salt thereof, wherein
$R^1$ represents phenyl or indanyl, which phenyl is optionally substituted with one or more substituents independently selected from the group consisting of alkyl, halo, trifluoromethyl, trifluoromethoxy, hydroxy, alkoxy, cyano, nitro and amino; and $R^2$, $R^3$ and $R^4$ independently of each other, represent hydrogen, alkyl, hydroxy-alkyl, alkenyl, alkynyl, halo, trifluoromethyl, trifluoromethoxy, hydroxy, alkoxy, cyano, nitro or amino.

In one embodiment of the invention, in formula (I), $R^1$ represent phenyl optionally substituted with one or more substituents independently selected from the group consisting of alkyl, halo, trifluoromethyl, trifluoromethoxy, hydroxy, alkoxy, cyano, nitro and amino. In another embodiment, $R^1$ represent phenyl. In another embodiment, $R^1$ represent phenyl substituted with one or more substituents independently selected from the group consisting of alkyl, halo, trifluoromethyl, cyano, nitro and amino. In another embodiment, $R^1$ represent phenyl substituted with one substituent selected from the group consisting of alkyl, halo, trifluoromethyl, cyano, nitro and amino. In another embodiment, $R^1$ represent phenyl substituted with two substituents independently selected from the group consisting of alkyl, halo, trifluoromethyl, cyano, nitro and amino. In another embodiment, $R^1$ represent phenyl substituted with one substituent selected from the group consisting of alkyl and halo. In another embodiment, $R^1$ represent phenyl substituted with alkyl, e.g. methyl. In another embodiment, $R^1$ represent phenyl substituted with halo, e.g. chloro. In another embodiment, $R^1$ represent phenyl substituted with two substituents independently selected from the group consisting of alkyl and halo. In another embodiment, $R^1$ represent phenyl substituted two times with alkyl, e.g methyl. In another embodiment, $R^1$ represent phenyl substituted two times with halo.

In another embodiment of the invention, in formula (I), $R^1$ represent indanyl.

In another embodiment of the invention, in formula (I), $R^2$, $R^3$ and $R^4$ independently of each other, represent hydrogen, alkyl, halo, trifluoromethyl, nitro or amino. In another embodiment, $R^2$, $R^3$ and $R^4$ independently of each other, represent hydrogen or alkyl. In another embodiment, $R^2$, $R^3$ and $R^4$ independently of each other, represent hydrogen or halo. In another embodiment, $R^2$, $R^3$ and $R^4$ independently of each other, represent hydrogen or trifluoromethyl. In another embodiment, $R^2$, $R^3$ and $R^4$ independently of each other, represent hydrogen or nitro. In another embodiment, $R^2$, $R^3$ and $R^4$ independently of each other, represent hydrogen or amino.

In another embodiment of the invention, in formula (I), one of $R^2$, $R^3$ and $R^4$ represents hydrogen; and the other two of $R^2$, $R^3$ and $R^4$ independently of each other, represent alkyl, hydroxy-alkyl, alkenyl, alkynyl, halo, trifluoromethyl, trifluoromethoxy, hydroxy, alkoxy, cyano, nitro or amino. In another embodiment, one of $R^2$, $R^3$ and $R^4$ represents hydrogen; and the other two of $R^2$, $R^3$ and $R^4$ independently of each other, represent alkyl, halo, trifluoromethyl, nitro or amino. In another embodiment, one of $R^2$, $R^3$ and $R^4$ represents hydrogen; and the other two of $R^2$, $R^3$ and $R^4$ represent alkyl. In another embodiment, one of $R^2$, $R^3$ and $R^4$ represents hydrogen; and the other two of $R^2$, $R^3$ and $R^4$ represent halo. In another embodiment, one of $R^2$, $R^3$ and $R^4$ represents hydrogen; and the other two of $R^2$, $R^3$ and $R^4$ represent trifluoromethyl. In another embodiment, one of $R^2$, $R^3$ and $R^4$ represents hydrogen; and the other two of $R^2$, $R^3$ and $R^4$ represent nitro. In another embodiment, one of $R^2$, $R^3$ and $R^4$ represents hydrogen; and the other two of $R^2$, $R^3$ and $R^4$ represent amino. In another embodiment, $R^3$ represents hydrogen and $R^2$ and $R^4$ represent alkyl, e.g. methyl. In another embodiment, $R^3$ represents hydrogen and $R^2$ and $R^4$ represent halo, e.g. chloro.

In another embodiment of the invention, in formula (I), two of $R^2$, $R^3$ and $R^4$ represent hydrogen; and the remaining one of $R^2$, $R^3$ and $R^4$ represents alkyl, hydroxyalkyl, alkenyl, alkynyl, halo, trifluoromethyl, trifluoromethoxy, hydroxy, alkoxy, cyano, nitro or amino. In another embodiment, two of $R^2$, $R^3$ and $R^4$ represent hydrogen; and the remaining one of $R^2$, $R^3$ and $R^4$ represents alkyl, halo, trifluoromethyl, nitro or amino. In another embodiment, two of $R^2$, $R^3$ and $R^4$ represent hydrogen; and the remaining one of $R^2$, $R^3$ and $R^4$ represents alkyl. In another embodiment, two of $R^2$, $R^3$ and $R^4$ represent hydrogen; and the remaining one of $R^2$, $R^3$ and $R^4$ represents halo. In another embodiment, two of $R^2$, $R^3$ and $R^4$ represent hydrogen; and the remaining one of $R^2$, $R^3$ and $R^4$ represents trifluoromethyl. In another embodiment, two of $R^2$, $R^3$ and $R^4$ represent hydrogen; and the remaining one of $R^2$, $R^3$ and $R^4$ represents nitro. In another embodiment, two of $R^2$, $R^3$ and $R^4$ represent hydrogen; and the remaining one of $R^2$, $R^3$ and $R^4$ represents amino.

In another embodiment of the invention, in formula (I), $R^1$ represents phenyl or indanyl, which phenyl is optionally substituted with one or more substituents independently selected from the group consisting of alkyl and halo, and one of $R^2$, $R^3$ and $R^4$ represents hydrogen; and the other two of $R^2$, $R^3$ and $R^4$ represent alkyl.

In another embodiment of the invention, in formula (I), $R^1$ represent phenyl substituted with halo; and one of $R^2$, $R^3$ and $R^4$ represents hydrogen; and the other two of $R^2$, $R^3$ and $R^4$ represent alkyl.

In another embodiment of the invention, in formula (I), $R^1$ represent phenyl substituted with halo; $R^3$ represents hydrogen and $R^2$ and $R^4$ represent alkyl.

In another embodiment of the invention, in formula (I), $R^1$ represent indanyl; and one of $R^2$, $R^3$ and $R^4$ represents hydrogen; and the other two of $R^2$, $R^3$ and $R^4$ represent alkyl.

In another embodiment of the invention, in formula (I), $R^1$ represent indanyl; $R^3$ represents hydrogen and $R^2$ and $R^4$ represent alkyl.

In another embodiment of the invention, the compound of the invention is: (4-Chloro-phenyl)-[2-(3,5-dimethyl-pyrazol-1-yl)-6-morpholin-4-yl-pyrimidin-4-yl]-amine; [2-(3,5-Dimethyl-pyrazol-1-yl)-6-morpholin-4-yl-pyrimidin-4-yl]-indan-2-yl-amine; or any of its stereoisomers or any mixture of its stereoisomers, or a pharmaceutically acceptable salt thereof.

Any combination of two or more of the embodiments described herein is considered within the scope of the present invention.

Definition of Substituents

As used throughout the present specification and appended claims, the following terms have the indicated meaning:

The term "halo" or "halogen" shall mean fluorine, chlorine, bromine or iodine.

The term "alkyl" as used herein means a saturated, branched or straight hydrocarbon chain, e.g. from one to six carbon atoms ($C_{1-6}$-alkyl; lower alkyl), including pentyl, isopentyl, neopentyl, tertiary pentyl, hexyl and isohexyl. In another embodiment alkyl represents a $C_{1-4}$-alkyl group, including butyl, isobutyl, secondary butyl, and tertiary butyl. In another embodiment of this invention alkyl represents a $C_{1-3}$-alkyl group, which may in particular be methyl, ethyl, propyl or isopropyl.

The term "alkenyl" as used herein designates a carbon chain containing one or more double bonds, including di-enes, tri-enes and poly-enes. In another embodiment the alkenyl group of the invention comprises of from two to eight carbon atoms ($C_{2-8}$-alkenyl), e.g. from two to six carbon atoms ($C_{2-6}$-alkenyl), including at least one double bond. In another embodiment the alkenyl group of the invention is ethenyl; 1- or 2-propenyl; 1-, 2- or 3-butenyl, or 1,3-butenyl; 1-, 2-, 3-, 4- or 5-hexenyl, or 1,3-hexenyl, or 1,3,5-hexenyl; 1-, 2-, 3-, 4-, 5-, 6-, or 7-octenyl, or 1,3-octenyl, or 1,3,5-octenyl, or 1,3,5,7-octenyl.

The term "alkynyl" as used herein designates a straight or branched carbon chain containing one or more triple bonds, including di-ynes, tri-ynes and poly-ynes. In another embodiment the alkynyl group of the invention comprises of from two to eight carbon atoms ($C_{2-8}$-alkynyl), e.g. from two to six carbon atoms ($C_{2-6}$-alkynyl), including at least one triple bond. In another embodiment the alkynyl group of the invention is ethynyl; 1-, or 2-propynyl; 1-, 2-, or 3-butynyl, or 1,3-butadiynyl; 1-, 2-, 3-, 4-pentynyl, or 1,3-pentadiynyl; 1-, 2-, 3-, 4-, or 5-hexynyl, or 1,3-hexadiynyl or 1,3,5-hexatriynyl; 1-, 2-, 3-, 4-, 5- or 6-heptynyl, or 1,3-heptdiynyl, or 1,3,5-hepttriynyl; 1-, 2-, 3-, 4-, 5-, 6- or 7-octynyl, or 1,3-octdiynyl, or 1,3,5-octtriynyl, or 1,3,5,7-octtetraynyl.

The term "hydroxy" shall mean the radical —OH.
The term "cyano" shall mean the radical —CN.
The term "nitro" shall mean the radical —$NO_2$.
The term "amino" shall mean the radical —$NH_2$.
The term "alkoxy" as used herein refers to the radical —O-alkyl. Representative examples are methoxy, ethoxy, propoxy (e.g. 1-propoxy, 2-propoxy), butoxy (e.g. 1-butoxy, 2-butoxy, 2-methyl-2-propoxy), pentoxy (1-pentoxy, 2-pentoxy), hexoxy (1-hexoxy, 3-hexoxy), and the like.

The term "trihalomethyl" shall mean trifluoromethyl, trichloromethyl, and similar trihalo-substituted methyl groups.

The term "trihalomethoxy" shall mean trifluoromethoxyl, trichloromethoxy, and similar trihalo-substituted methoxy groups.

The term hydroxy-alkyl" as used herein designates an alkyl group as defined above, which hydroxy-alkyl group is substituted with one or more hydroxy groups. Examples of hydroxy-alkyl groups of the invention include 2-hydroxy-ethyl, 3-hydroxy-propyl, 4-hydroxy-butyl, 5-hydroxy-pentyl and 6-hydroxy-hexyl.

The term "optionally substituted" as used herein means that the groups in question are either unsubstituted or substituted with one or more of the substituents specified. When the group(s) in question are substituted with more than one substituent, the substituents may be the same or different.

Certain of the defined terms may occur more than once in the structural formulae, and upon such occurrence each term shall be defined independently of the other.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The terms "disease", "condition" and "disorder" as used herein are used interchangeably to specify a state of a patient which is not the normal physiological state of man.

The term "medicament" as used herein means a pharmaceutical composition suitable for administration of the pharmaceutically active compound to a patient.

The term "pharmaceutically acceptable" as used herein means suited for normal pharmaceutical applications, i.e. giving rise to no adverse events in patients etc.

The term "effective amount" as used herein means a dosage which is sufficient in order for the treatment of the patient to be effective compared with no treatment.

The term "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

Steric Isomers

It will be appreciated by those skilled in the art that the compounds of the present invention may exist in different stereoisomeric forms—including enantiomers, diastereomers and cis-trans-isomers.

The invention includes all such stereoisomers and any mixtures thereof including racemic mixtures.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Moreover, some of the chemical compounds of the invention being oximes, may thus exist in two forms, syn- and anti-form (Z- and E-form), depending on the arrangement of the substituents around the —C=N— double bond. A chemical compound of the present invention may thus be the syn- or the anti-form (Z- and E-form), or it may be a mixture hereof.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention, including compounds modified at one or more reactive or derivatizable groups of the parent compound. Of particular interest are compounds modified at a carboxyl group, a hydroxyl group, or an amino group. Examples of suitable derivatives are esters or amides.

The compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Methods of Preparation

The compounds of the invention may be prepared by conventional methods of chemical synthesis, e.g. those described in the working examples. The starting materials for the processes described in the present application are known or may readily be prepared by conventional methods from commercially available chemicals.

The end products of the reactions described herein may be isolated by conventional techniques, e.g. by extraction, crystallisation, distillation, chromatography, etc.

Biological Activity

The compounds of the invention may be tested for their usefulness as potassium channel modulating agents e.g. such as described in WO 2006/100212.

The compounds of the invention are capable of selectively modulating SK1, SK2 and/or SK3 channels. Therefore, in another aspect, the invention relates to the use of the compounds of the invention for the manufacture of medicaments, which medicament may be useful for the treatment or alleviation of a disease or a disorder associated with the activity of potassium channels, e.g. SK channels, e.g. SK1, SK2 and/or SK3 channels.

In another embodiment, the disease or a disorder associated with the activity of potassium channels is a respiratory disease, epilepsy, convulsions, seizures, absence seizures, vascular spasms, coronary artery spasms, renal disorders, polycystic kidney disease, bladder spasms, overactive bladder (OAB), urinary incontinence, bladder outflow obstruction, interstitiel cystitis (IC), erectile dysfunction, gastrointestinal dysfunction, secretory diarrhoea, ischaemia, cerebral ischaemia, ischaemic heart disease, angina pectoris, coronary heart disease, autism, ataxia, traumatic brain injury, Parkinson's disease, dyskinesia, bipolar disorder, psychosis, schizophrenia, anxiety, depression, mania, mood disorders, dementia, memory and attention deficits, Alzheimer's disease, amyotrophic lateral sclerosis (ALS), dysmenorrhea, narcolepsy, Reynaud's disease, intermittent claudication, Sjogren's syndrome, arrhythmia, hypertension, myotonic muscle dystrophia, spasticity, xerostomi, diabetes type II, hyperinsulinemia, premature labour, hair loss, cancer, irritable bowel syndrome (IBS), immune suppression, migraine or pain, e.g. pelvic pain or abdominal pain, addiction, e.g. drug addiction, drug abuse, cocaine abuse, nicotine abuse, tobacco abuse, alcohol addiction or alcoholism, or withdrawal symptoms caused by the termination of abuse of chemical substances, in particular opioids, heroin, cocaine and morphine, benzodiazepines and benzodiazepine-like drugs, and alcohol.

In another embodiment the disease or a disorder associated with the activity of potassium channels is a respiratory disease, urinary incontinence, erectile dysfunction, anxiety, epilepsy, psychosis, schizophrenia, amyotrophic lateral sclerosis (ALS) or pain.

In another embodiment the disease or a disorder associated with the activity of potassium channels is a respiratory disease, in particular asthma, cystic fibrosis, chronic obstructive pulmonary disease (COPD) or rhinorrhea.

In another embodiment the disease or a disorder associated with the activity of potassium channels is overactive bladder, e.g. urinary incontinence.

In another embodiment the disease or a disorder associated with the activity of potassium channels is epilepsy, seizures, absence seizures or convulsions.

In another embodiment the disease or a disorder associated with the activity of potassium channels is schizophrenia.

In another embodiment the disease or a disorder associated with the activity of potassium channels is addiction.

In another embodiment the disease or a disorder associated with the activity of potassium channels is Parkinson's disease.

In another embodiment the disease or a disorder associated with the activity of potassium channels is pain.

The compounds tested showed a biological activity determined as described herein in the micromolar and sub-micromolar range, i.e. of from below 1 to above 100 µM e.g. from below 0.1 to about 10 µM.

Pharmaceutical Compositions

In yet another aspect the invention provides novel pharmaceutical compositions comprising a therapeutically effective amount of the compounds of the invention.

While a compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers and/or diluents.

In another embodiment, the invention provides pharmaceutical compositions comprising the compound of the invention, or a pharmaceutically acceptable salt or compound thereof, together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The derivates of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the chemical compound according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

In one embodiment, the invention provides tablets or capsules for oral administration In another embodiment, the invention provides and liquids for intravenous administration and continuous infusion.

Further details on techniques for formulation and administration may be found in the latest edition of *Remington's Pharmaceutical Sciences* (Maack Publishing Co., Easton, Pa.).

A therapeutically effective dose refers to that amount of active ingredient which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions which exhibit large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated and the route of administration, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, e.g. from about 1 to about 100 mg, e.g. from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Other ranges are from about 0.1 µg/kg to about 10 mg/kg/day i.v., and from about 1 µg/kg to about 100 mg/kg/day p.o.

Methods of Therapy

In another aspect the invention provides a method for the prevention, treatment or alleviation of a disease or a disorder or a condition of a living animal body, including a human, which disease, disorder or condition is responsive to modulation of potassium channels, in particular SK channels, and which method comprises comprising administering to such a living animal body, including a human, in need thereof a therapeutically-effective amount of a compound of the invention.

The indications contemplated according to the invention are those stated above.

It is at present contemplated that suitable dosage ranges are 0.1 to 1000 milligrams daily, 10-500 milligrams daily, or 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Other ranges are from about 0.001 to about 1 mg/kg i.v. and from about 0.1 to about 10 mg/kg p.o.

EXAMPLES

The following examples refer to intermediate compounds and final products for general formula (I) identified in the specification. The preparation of the compounds of general formula (I) of the present invention is described in detail using the following examples. Occasionally, the reaction may not be applicable as described to each compound included within the disclosed scope of the invention. The compounds for which this occurs will be readily recognized by those skilled in the art. In these cases the reactions can be successfully performed by conventional modifications known to those skilled in the art, which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials.

Example 1

4,6-Dichloro-2-methanesulfonyl-pyrimidine

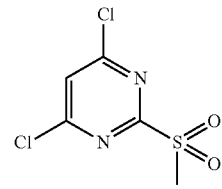

A solution of 4,6-dichloro-2-(methylthio)pyrimidine (48.3 g, 247 mmol) in dichloromethane (1 L) was cooled on an ice bath. 3-Chloroperoxybenzoic acid (152 g, 619 mmol) was added portion-wise keeping the temperature below 10° C. The solution was allowed to warm to room-temperature and stirred over-night. The mixture was diluted with dichloromethane (2 L) and treated with an aqueous solution of sodium thiosulphate and sodium hydrogen carbonate (600 mL). The resulting mixture was stirred over-night. The phases were separated and the organic layer was washed with sodium hydrogencarbonate (500 mL) and brine (1 L), dried over sodium sulphate, filtrated and concentrated in vacuo. The resulting yellow solid was stirred with ether and 4,6-dichloro-2-methanesulfonyl-pyrimidine (32.6 g, 58%) was collected by filtration as a white solid.

Example 2

4,6-Dichloro-2-(3,5-dimethyl-pyrazol-1-yl)-pyrimidine

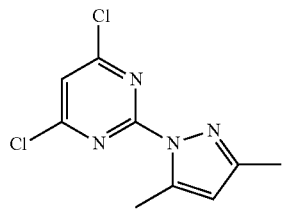

A suspension of 3,5-dimethylpyrazole (3.9 g, 40.7 mmol) and sodium hydride (60% in mineral oil, 1.7 g) in dichloromethane (50 mL) was added dropwise to a cooled (−78° C.) solution of 4,6-dichloro-2-methanesulfonyl-pyrimidine (10 g, 38.7 mmol) in dichloromethane (200 mL). The mixture was stirred at −78° C. for one hour. The reaction was carefully quenched at the same temperature by addition of water (150 mL). The mixture was allowed to warm to room-temperature. Brine (150 mL) was added and the phases were separated. The aqueous phase was extracted with dichloromethane (4×200 mL). The combined organic layers were washed with brine, dried over sodium sulphate, filtrated and concentrated in vacuo. The crude product was purified by flash chromatography (ethyl acetate/heptane as eluent) to give 4,6-dichloro-2-(3,5-dimethyl-pyrazol-1-yl)-pyrimidine (5.5 g, 59%) as a white crystalline compound.

Example 3

[6-Chloro-2-(3,5-dimethyl-pyrazol-1-yl)-pyrimidin-4-yl]-(4-chloro-phenyl)-amine

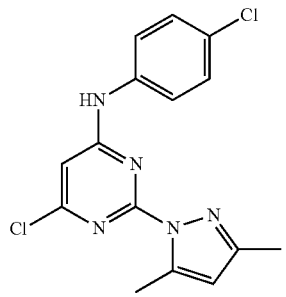 [SMILES: Cc1cc(C)n(-c2nc(Cl)cc(Nc3ccc(Cl)cc3)n2)n1]

4,6-Dichloro-2-(3,5-dimethyl-pyrazol-1-yl)-pyrimidine (3.5 g, 14.4 mmol) and 4-chloroaniline (3.7 g, 28.8 mmol) were suspended in water (120 mL) and ethanol (17 mL). Concentrated hydrochloric acid (0.6 mL, 7.2 mmol) was added and the mixture was heated to 88° C. over-night. Additional 4-chloroaniline (918 mg) was added and stirring was continued for six hours. The mixture was cooled to room temperature and diluted with water. The resulting solid was collected by filtration to give [6-chloro-2-(3,5-dimethylpyrazol-1-yl)-pyrimidin-4-yl]-(4-chloro-phenyl)-amine (4.8 g, 99%) as a white solid.

[6-Chloro-2-(3,5-dimethyl-pyrazol-1-yl)-pyrimidin-4-yl]-indan-2-yl-amine

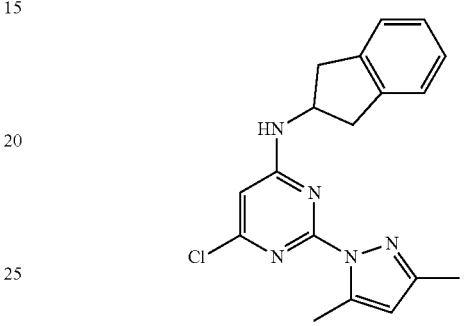

Was prepared according to example 3 from 4,6-dichloro-2-(3,5-dimethyl-pyrazol-1-yl)-pyrimidine and 2-aminoindan.

Example 4

(4-Chloro-phenyl)-[2-(3,5-dimethyl-pyrazol-1-yl)-6-morpholin-4-yl-pyrimidin-4-yl]-amine (Compound 4.1)

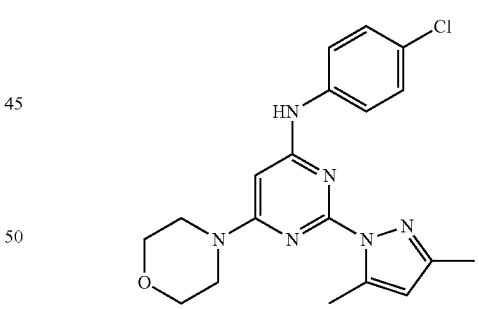

A mixture of [6-chloro-2-(3,5-dimethyl-pyrazol-1-yl)-pyrimidin-4-yl]-(4-chlorophenyl)-amine (125 mg, 0.37 mmol) and morpholine (0.32 mL, 3.74 mmol) in 1-methyl-2-pyrrolidinone (4 mL) was stirred for one hour at 110° C. The reaction mixture was allowed to cool down to room temperature, acidified with aqueous hydrochloric acid (1 M) and extracted with ethyl acetate. The combined organic phases were washed with brine, dried over sodium sulphate, filtrated and concentrated in vacuo. The crude product was purified by flash chromatography (dichloromethane/methanol as eluent) to give (4-chloro-phenyl)-[2-(3,5-dimethyl-pyrazol-1-yl)-6-morpholin-4-yl-pyrimidin-4-yl]-amine (92 mg, 64%) as a white solid. Mp. 186-187° C.

LC-ESI-HRMS of [M+H]+ shows 385.1545 Da. Calc. 385.154362 Da, dev. 0.4 ppm

[2-(3,5-Dimethyl-pyrazol-1-yl)-6-morpholin-4-yl-pyrimidin-4-yl]-indan-2-yl-amine (Compound 4.2)

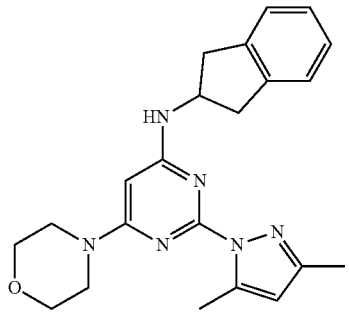 [SMILES: Cc1cc(C)n(-c2nc(NC3Cc4ccccc4C3)cc(N3CCOCC3)n2)n1]

Was prepared according to example 4 from [6-chloro-2-(3,5-dimethyl-pyrazol-1-yl)-pyrimidin-4-yl]-indan-2-yl-amine and morpholine. Mp. 66-70° C.

LC-ESI-HRMS of [M+H]+ shows 391.2234 Da. Calc. 391.224089 Da, dev. −1.8 ppm

Example 5

Biological Activity

This example demonstrates the biological activity of a compound representative of the invention (Compound 4.1). The ionic current through small-conductance $Ca^{2+}$-activated $K^+$ channels (SK channels, subtype 3) is recorded using the whole-cell configuration of the patch-clamp technique in a classic patch-clamp set-up using HEK293 tissue culture cells expressing hSK3 channels as described in e.g. WO 2006/100212

The $SC_{100}$ value determined is defined as the Stimulating Concentration required for increasing the baseline current by 100%. The $SC_{100}$ value determined for Compound 4.1 of the invention was 0.022±0.013 μM, which is an indication of its SK3 activating properties.

The invention claimed is:

1. A compound of formula (I)

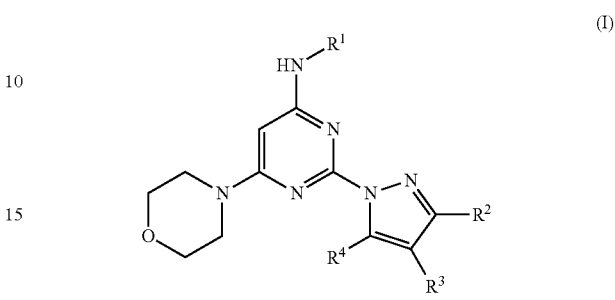

or a pharmaceutically acceptable salt thereof, wherein
$R^1$ represents phenyl or indanyl, which phenyl is optionally substituted with one or more substituents independently selected from alkyl and halo; and
one of $R^2$, $R^3$ and $R^4$ represent hydrogen; and the other two of $R^2$, $R^3$, and $R^4$ represent alkyl.

2. The compound according to claim 1, or a pharmaceutically acceptable salt thereof, wherein $R^1$ represents phenyl which is optionally substituted with halo.

3. The compound according to claim 1, or a pharmaceutically acceptable salt thereof, wherein $R^1$ represents indanyl.

4. The compound of claim 1, which is:
  (4-Chloro-phenyl)-[2-(3,5-dimethyl-pyrazol-1-yl)-6-morpholin-4-yl-pyrimidin-4-yl]-amine;
  [2-(3,5-Dimethyl-pyrazol-1-yl)-6-morpholin-4-yl-pyrimidin-4-yl]-indan-2-yl-amine; or
  or a pharmaceutically acceptable salt thereof.

5. A pharmaceutical composition comprising a therapeutically effective amount of a compound according to claim 1 or a pharmaceutically acceptable salt thereof, together with at least one pharmaceutically-acceptable carrier or diluent.

* * * * *